United States Patent

Ford et al.

[11] Patent Number: 5,277,493
[45] Date of Patent: Jan. 11, 1994

[54] ANALYTICAL SAMPLE PREPARATION SYSTEM

[75] Inventors: Gordon C. Ford, St. Joseph; Peter M. Willis, Benton Harbor, both of Mich.

[73] Assignee: Leco Corporation, St. Joseph, Mich.

[21] Appl. No.: 846,814

[22] Filed: Mar. 6, 1992

Related U.S. Application Data

[63] Continuation-in-part of Ser. No. 664,052, Mar. 1, 1991.

[51] Int. Cl.$^5$ ............. B01F 15/06; B01F 11/00
[52] U.S. Cl. ................. 366/216; 366/144; 366/215; 366/217
[58] Field of Search ............ 65/178; 73/863; 249/120, 137; 266/48, 65, 240, 276; 366/208, 209, 210, 211, 215, 216, 217, 218, 219, 144; 422/104; 425/160, 256, 257, 258, 259; 414/419-421

[56] References Cited

U.S. PATENT DOCUMENTS

| 2,804,777 | 9/1957 | Kerr-Lawson | 366/217 |
|---|---|---|---|
| 3,437,317 | 4/1969 | Micin | 366/211 |
| 3,451,794 | 6/1969 | Patterson | 65/178 |
| 3,757,961 | 9/1973 | Jacobs | 414/751 |
| 3,890,089 | 6/1975 | Matocha | 432/11 |
| 4,045,202 | 8/1977 | Claisse | 65/178 |
| 4,138,209 | 2/1979 | Bahr | 425/160 |
| 4,317,560 | 3/1982 | Troyer | 266/48 |
| 4,329,136 | 5/1982 | Willay | 425/174.8 |
| 4,563,146 | 1/1986 | Kelly | 266/240 |
| 4,609,392 | 9/1986 | Claisse | 65/178 |
| 5,055,263 | 10/1991 | Meltzer | 422/104 |
| 5,167,928 | 12/1992 | Kelly | 366/208 |

FOREIGN PATENT DOCUMENTS

2369388 2/1989 Australia.
2248479 5/1975 France.
1527321 10/1978 United Kingdom.

OTHER PUBLICATIONS

"Look to the Leader, in Claisse Fluxer-Bis!," Corporation Scientifique Claisse, Inc., 8 pages Instruction Manual for FX-100 and FX-200 available from Leco Corporation, pp. 6 and S7.

Primary Examiner—Timothy F. Simone
Assistant Examiner—Terrence R. Till
Attorney, Agent, or Firm—Price, Heneveld, Cooper, DeWitt and Litton

[57] ABSTRACT

An apparatus for melting samples in crucibles above burners while moving the crucibles to mix the contents. The crucibles are supported by movable shafts on a movable subframe. The shafts can oscillate in a horizontal plane to mix the contents of the crucible. The subframe can also oscillate vertically to mix the contents of the crucible. The crucible mixing pattern is the sum of the horizontal and the vertical motion applied to the crucible. The crucible can be moved back away from the burner to add additional material to the crucible. The crucible can be moved forward, away from the burner, to pour the melted sample into either a heated casting dish or a container containing a solution. Nothing is added to or poured from the crucible while over the burners.

10 Claims, 7 Drawing Sheets

ANALYTICAL SAMPLE PREPARATION SYSTEM

CROSS-REFERENCE TO RELATED APPLICATION

The present application is a continuation-in-part of application Ser. No. 07/664,052 filed Mar. 1, 1991, entitled ANALYTICAL SAMPLE PREPARATION SYSTEM. The present application is assigned to the assignee of the parent application.

BACKGROUND OF THE INVENTION

The apparatus of the present invention is commonly referred to as a "fluxer." In this type of apparatus, a sample is heated to a molten state in a crucible and is then either poured into a casting dish to prepare a solid glass-like disc for analysis by instrumental techniques or the heated sample is poured into an acid solution contained in a beaker for analysis. Some of the devices known in the past would add materials to the crucibles while the crucibles were above and being heated by the burners. Also, the molten contents of the crucible was poured into a casting dish above the burner, the burner being used to heat the crucible and the casting dish. A fluxer usually contained several burners and facilities for supporting several crucibles. If the apparatus was prepared to add a wetting agent to the molten sample in the crucible, and a crucible was not in place, the wetting agent could be dumped directly into the burner. Likewise, if the laboratory technician forgot to install a casting dish into the apparatus and the apparatus dumped the contents of the crucible into the absent casting dish, the contents would be poured into the burner. In either case, the burner would be seriously damaged or totally destroyed by the molten material.

It is also known in the operation of a fluxer that the crucible should be agitated vigorously in order to properly mix the molten sample in the crucible. Various complicated mechanical arrangements have been provided for moving the crucible while it is being heated and, in some cases, a shaped crucible was used to cause the material to separate and remix as it was poured from one side of the crucible bottom to the other.

SUMMARY OF THE INVENTION

In accordance with the present invention, an apparatus is provided for supporting a molten sample in a crucible and for agitating or mixing the contents of the crucible while it is being heated. If a material is to be added to the crucible, the crucible is moved away from the burner for the addition of the material. When the molten contents of the crucible are to be poured into a casting dish or beaker of acid solution, the crucible is again moved away from the burner before the molten material is poured from the crucible. No materials are added to or poured from the crucibles while the crucibles are over the burners. Also, an improved system is provided for mixing the contents of the crucible which provides input in the horizontal or X-direction and a simultaneous vertical or Y-direction input so that the sum of the forces applied to the crucible cause it to move to mix the contents thereof. The X- and Y-forces applied to the crucible are variable so that many different mixing patterns are available. The apparatus of the present invention also utilizes plug-in subassemblies for supporting and heating the casting dishes and a separate subassembly, preferably equipped with magnetic stirring devices to stir the acid solutions as the molten material is added.

BRIEF DESCRIPTION OF THE DRAWINGS

FIG. 2a is a top plan view of a crucible holder of a sample preparation instrument embodying the invention;

DETAILED DESCRIPTION OF THE PREFERRED EMBODIMENTS

The improved fluxer of the present invention is indicated by the number 20. The apparatus has an open front, a right sidewall 21, a left sidewall 23, a back wall 25 which is connected to the right and left sidewalls, and a bottom plate 27. Three burners 29, 31 and 33 extend upwardly from bottom plate 27. Each burner has an igniter 35 and a thermocouple 37 for lighting and monitoring the temperature of the associated burner.

A first journal block 39 is pivotally mounted on the inside surface of sidewall 21. A second journal block 41 is pivotally mounted on the inside surface of left sidewall 23. An elongated shaft 43 is slidably mounted in an upper aperture 45 in journal block 39. Shaft 43 has a rack gear 47 on its upper surface. Shaft 43 supports a balance 49 at one end and a movable subframe 51 on the opposite side of journal block 39 from counter balance weight 49. A second rack 53 extends through aperture 55 in journal block 39. Rack 53 is fastened to movable subframe 51. A pinion gear 57 causes rack 53 to move and, in turn, the subframe to move.

Journal block 41 is pivotally mounted on the inside of sidewall 23. A shaft 59, similar to shaft 43, extends through journal block 41 and is fastened to counter balance 49. Shafts 43 and 59 are fastened to counter balance 49 by a pair of fastener members 61 and 63. A second shaft 65 is also supported in journal block 41. Shaft 65 is preferably square in configuration. A driving gear 67 is mounted on the end of shaft 65 behind front panel 69 of movable subframe 51. Subframe 51 has a front panel 69 which supports three movable shafts 71. The shafts 71 are mounted in bushings 73. Because of the heat involved in the operation of the machine, the components are made of stainless steel with the exception of the bushings which are bronze. Shafts 71 support crucible holders 75 which are clamped to shafts 71 by threaded fasteners 77. Crucible holders 75 (FIG. 2a) are described in copending application Ser. No. 07/644,052.

Behind panel 69 each shaft 71 supports a sprocket 79. A continuous chain 81 is trained over driving gear 67 and each of sprockets 79.

A pair of journal blocks 83 are mounted on the back of panel 69. A cross shaft 85 is supported by each of the journal blocks. Cross shaft 85 has a pinion gear 87 attached to each end. Pinion gears 87 mesh with the rack-like teeth on the top of shafts 43 and 59 and prevent subframe 51 from cocking or canting as it is moved backward and forward by rack 53 and pinion gear 57.

A first drive motor 91 is operatively connected to square shaft 65 by a continuous chain 93 which is trained over a sprocket 95 on motor 91, and a sprocket 97 mounted on square shaft 65. A shaft encoder 99 is coupled to motor 91. Motor 91 is preferably a servo motor and the shaft encoder provides output pulses or counts indicating the motion of sprocket 95 on the output of motor 91. Motor 91 causes sprocket gear and square shaft 65 to oscillate which, in turn, causes driven gear 67 to oscillate. Driven gear 67 is connected to sprockets 79 on the end of each of the shafts 71 which causes shafts 71 to oscillate as chain 81 moves back and forth over the sprockets. Shafts 71 support the holders for the crucibles.

A second motor 101 is mounted on the outside of sidewall 21. Motor 101 is preferably a servo motor and has a shaft encoder 103 which provides a pulse for each step of the rotation of the motor. A sprocket 105 is attached to the output of motor 101. A continuous chain 107 is trained over sprocket 105 and a sprocket 109 in clutch assembly 110. Sprocket 109 is mounted on a shaft 111 upon which pinion gear 57 is mounted.

Figure 5:
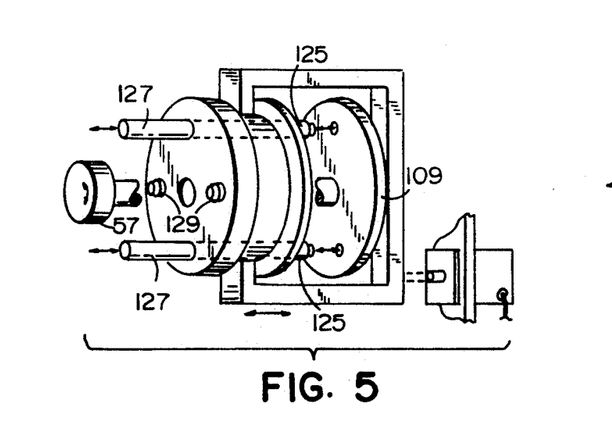
FIG. 5 is a partial broken away view of the clutch assembly.
Figure 6:
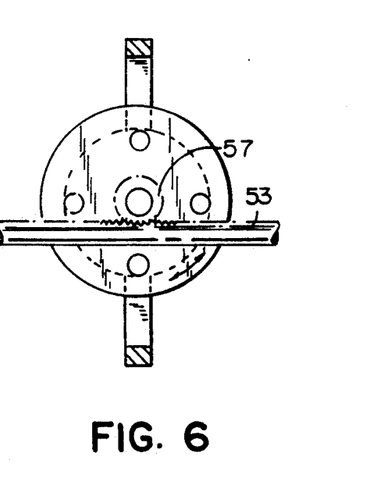
FIG. 6 shows the movement of the clutch disc for moving the junction block and the pinion gear.
Figure 7:
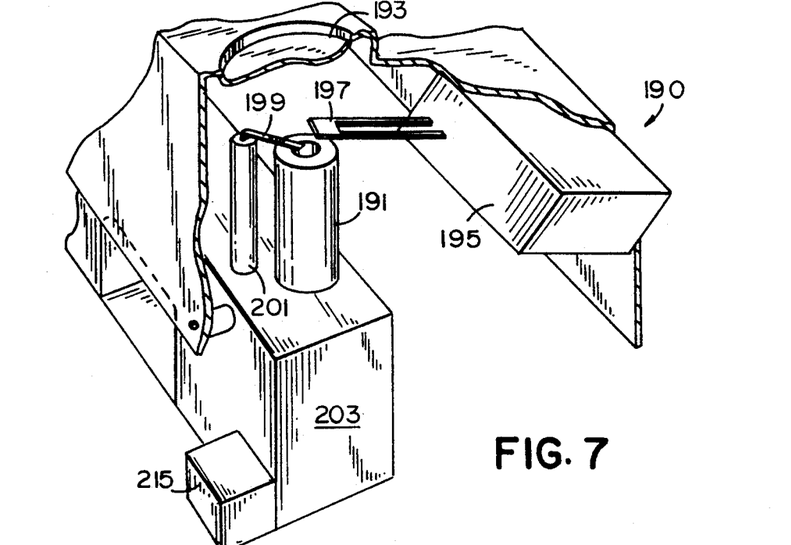
FIG. 7 is a fragmentary perspective view of the casting dish subassembly.
Figure 8:
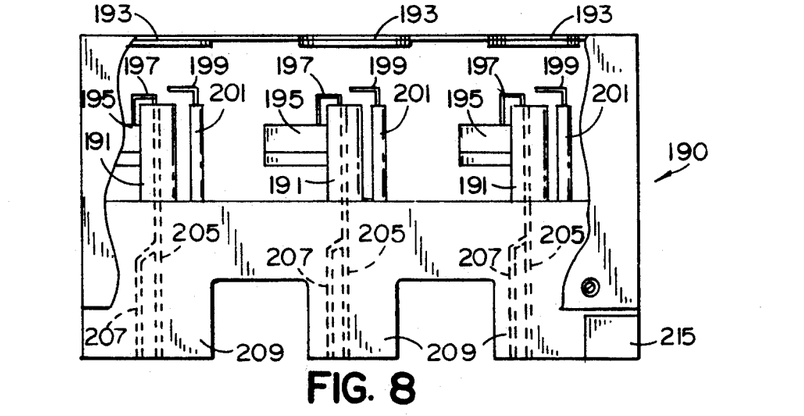
FIG. 8 is a elevational view of the casting dish subassembly.
Figure 9:
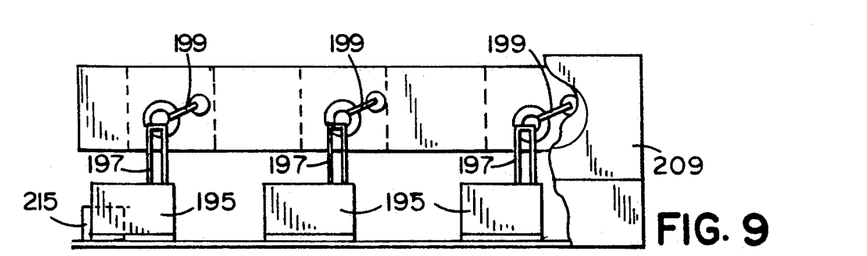
FIG. 9 is a top plan view of the casting dish subassembly.
Figure 10:
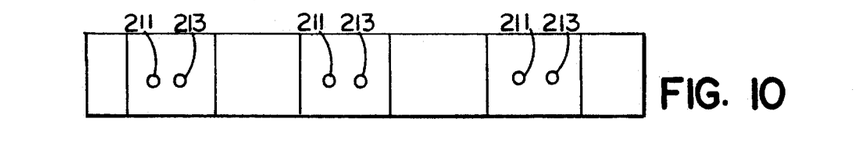
FIG. 10 is a bottom plan view of the casting dish assembly.
Figure 11:
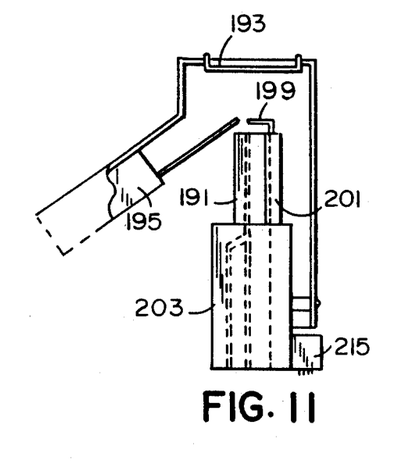
FIG. 11 is a side elevational view of the casting dish subassembly.
Figure 12:
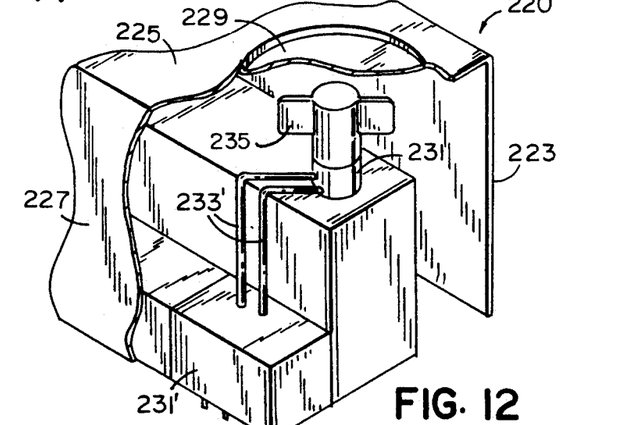
FIG. 12 is a fragmentary perspective view of the subassembly used with an acid solution.
Figure 13:
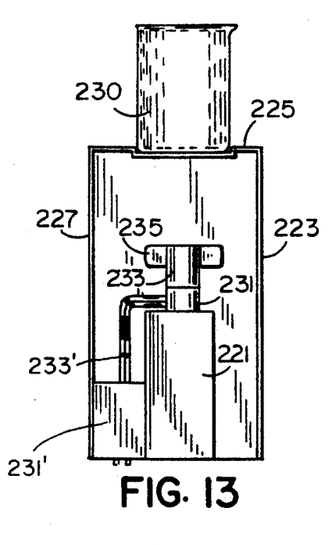
FIG. 13 is a side elevational view of the acid solution subassembly.
Figure 14:
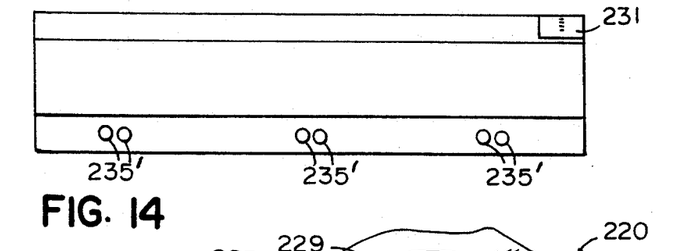
FIG. 14 is a bottom plan view of the acid solution subassembly.
Figure 15:
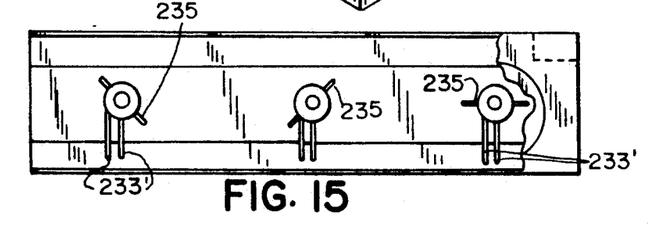
FIG. 15 is a top plan view of the acid solution subassembly.

Clutch assembly 110 has an outer frame 113 (FIGS. 2, 3 and 5) which attaches the clutch assembly to the outside of sidewall 21. Within frame 113 a substantially C-shaped movable member 115 is mounted. A pneumatic cylinder 117 is connected by a shaft 119 to movable member 115. Movable member 115 has a pair of opposed gripping faces 121 which grip clutch member 123.

Clutch member 123 is made of brass and supports three sets of steel pins. A first set of pins 125 are for connecting clutch 123 to sprocket gear 109. When so connected, pins 125 positioned in apertures 126 in journal block 39 cause the journal block to oscillate as determined by servo motor 101. When the clutch plate moves to the left, as shown in the figures, the third pin 129 enters apertures 131 on the outside of sidewall 21 which locks the clutch assembly, preventing any further movement of the frame and journal blocks 39 and 41. Sprocket gear 109 and shaft 111 can now rotate pinion 57 to cause subframe 51 to move forward or backward in the apparatus.

Journal blocks 39 and 41, shafts 43 and 59, counter balance 49 and movable subframe 51 make up a major movable frame 140. Frame 140 can oscillate vertically to mix the components in the crucible and can be locked in a horizontal position so that the subframe 51 can move to the rear of the apparatus for the addition of materials to the crucibles, or toward the front of the apparatus so that the contents of the heated crucibles can be poured into either a casting dish or a beaker containing an acid solution for analysis.

First servo motor 91 and second servo motor 101 combine to cause the main frame 140 to oscillate up and down while the crucibles supported by shafts 71 are rocking back and forth in a horizontal plane. The extent of the vertical and horizontal motion applied to the crucibles can be varied by monitoring the shaft encoders 99 and 103 so that the motors 91 and 101 undergo either large or small excursions before stopping and reversing travel. Motors 91 and 101 can be controlled by the overall program for the operation of the machine, as set forth in the parent application, all of which is incorporated herein by reference.

Figure 19:
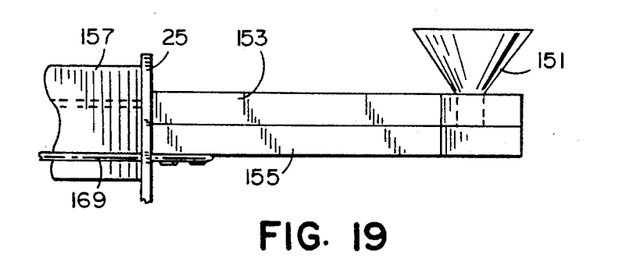
FIG. 19 is an elevational view of the apparatus used to add additional materials with the funnels closed.
Figure 20:
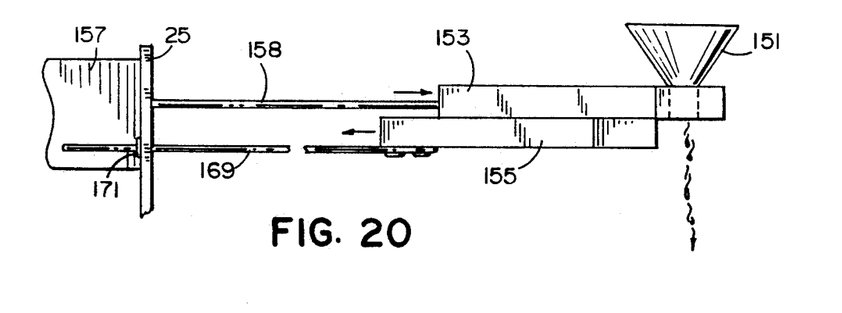
FIG. 20 is a view of the apparatus of FIG. 19 extended and with the funnel bottom opened.

It is common practice in the preparation of a sample for further analysis to add a wetting agent to the molten material contained in the crucibles. In the present apparatus, the wetting agents can be added to funnels 151 which are movably supported near the top of back wall 25 of the apparatus. The material addition apparatus includes an upper plate 153 which is in sliding contact with a lower plate 155. Funnels 151 have an open bottom (FIGS. 19 and 20) which is closed off by lower plate 155. A double pneumatic cylinder 157, which has a dual extending piston 158, only one of which is shown, attached to upper plate 153. Lower plate 155 is carried by upper plate 153. Upper plate 153 has a plurality of spaced slots 159 in which a large headed fastener 161 is attached to lower plate 155. Fasteners 161 hold lower plate 155 in tight sliding contact with upper plate 153.

As mentioned previously, movable subframe 51 can be caused to move to the rear of the machine to move the crucibles away from the burners for the addition of additives to the crucible. As the subframe moves toward the rear of the machine, it contacts a pin 163 in valve 165 which actuates double pneumatic cylinder 157 through line 167. Valve 165 functions, in effect, as an interlock and will not allow plates 153 and 155 to move until valve 165 has been opened, indicating that subframe 51 and the supported crucibles are at the rear of the apparatus. Once valve 165 is activated, dual pneumatic cylinder 157 moves plates 153 and 155, along with funnel 151 containing the additive material. Rods 169 are attached to the rear edge of lower plate 155. Each rod 169 has a stop 171 mounted thereon which stops the movement of plate 155, enabling plate 153 to continue to be driven forward, moving the bottoms of funnels 151 away from plate 155 and enabling the material contained in the funnels to drop into the heated crucibles. A heat shield and deflecting plate 173 extends across the width of the apparatus to prevent any possibility of any of the additive material, or any of the material in the crucible, accidentally landing on any wiring or plumbing. Slots 159 in plate 153 enable plate 153 to be driven beyond plate 155 to enable the bottoms of the funnels to be opened in a gate valve-like manner.

After the wetting agent is added to the crucibles, subassembly 51 is moved forward to return the crucibles over burners 29, 31 and 33. After the crucible is reheated, subframe 51 moves forward bringing the heated crucibles to the output station 180 where the molten material can either be poured into a casting dish to prepare a glass-like disc for analysis, or into a beaker containing an acid solution for further analysis.

At output station 180 either one of a pair of plug-in assemblies 190 or 220 can be mounted. Plug-in assembly 190 has three burners 191 for heating casting dishes 193 to prevent the sample material from being destroyed by thermal shock on pouring from a hot crucible into a cold casting dish. Each burner 191 has its own electrical igniter 195 which has a hot loop 197 extending out over the burner to ignite the combustible mixture of air and gas. Each burner has a flame detection wire 199 supported on an insulated post 201 for monitoring the status of the flame for heating casting dish 193. Burners 191 and flame detection supports 201 are supported on a solid frame 203 which has internal passages 205 and 207 for the air and fuel used in the burner. The passages for the air and gas are contained within spaced leg portions 209 of frame 203. Ports 211 and 213 are provided on the bottom of each leg 209 for connecting to the supply of air and gas in the apparatus. An electrical connector 215 is also provided on the plug-in assembly which connects the power source for igniters 195 and connects flame detectors 199 to the apparatus. The electrical plug 215 also contains circuitry to indicate to the control system of the apparatus that the casting dish assembly is in position and that the solenoid valves for the air and gas can be activated.

When the molten sample in the crucible is to be poured into a beaker containing an acid solution, separate subassembly 220 is inserted into the apparatus. Subassembly 220 has a base 221 which supports a vertical metal plate 223 which has a turned-over top section 225 and a downwardly turned edge 227. Top surface 225 has spaced recessed portions 229 for centering a beaker 230 over electric motor 231 which has an output shaft 233 supporting a bar magnet 235. The bottom of recess 229 is preferably made of a magnetic permeable material, such as stainless steel. The stainless steel will permit the magnetic field from the rotating bar magnet to act along with a bar magnet contained in the beaker to stir the solution. The plug-in assembly has an electrical connector 231' for providing power through electrical conductors 233' for driving magnetic stirring motor 231. The assembly also has plugs 235' for closing off the air and combustible gas inlets to the subassembly. When electrical plug 231' is connected to the apparatus, the connections in plug 231' enable the apparatus to determine that the magnetic stirring motors are in position, that the air and gas solenoids are not to be activated, and that the thermocouple and igniter circuits are disconnected.

Figure 1:
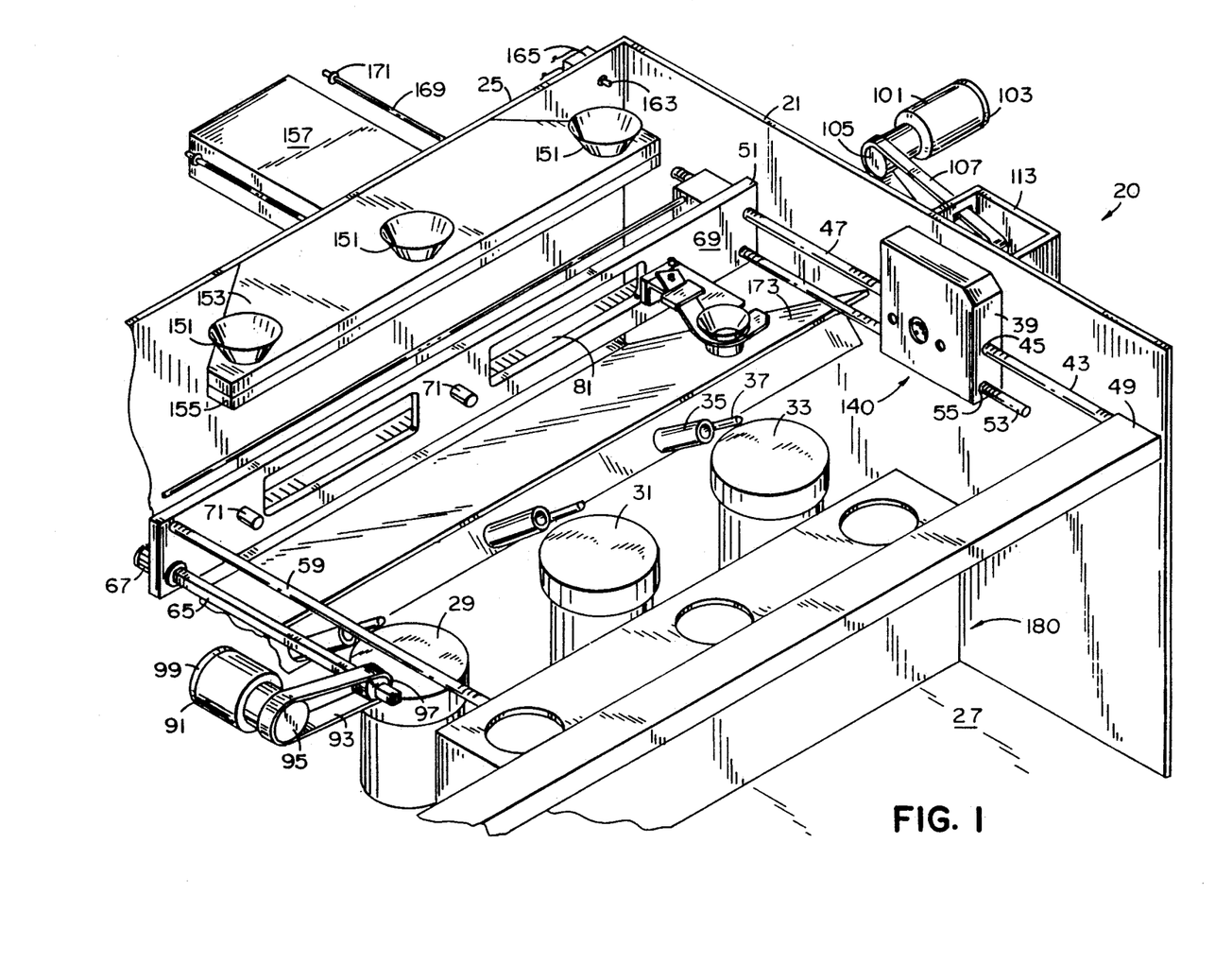
FIG. 1 is a fragmentary perspective view of the apparatus showing the main components.
Figure 2:
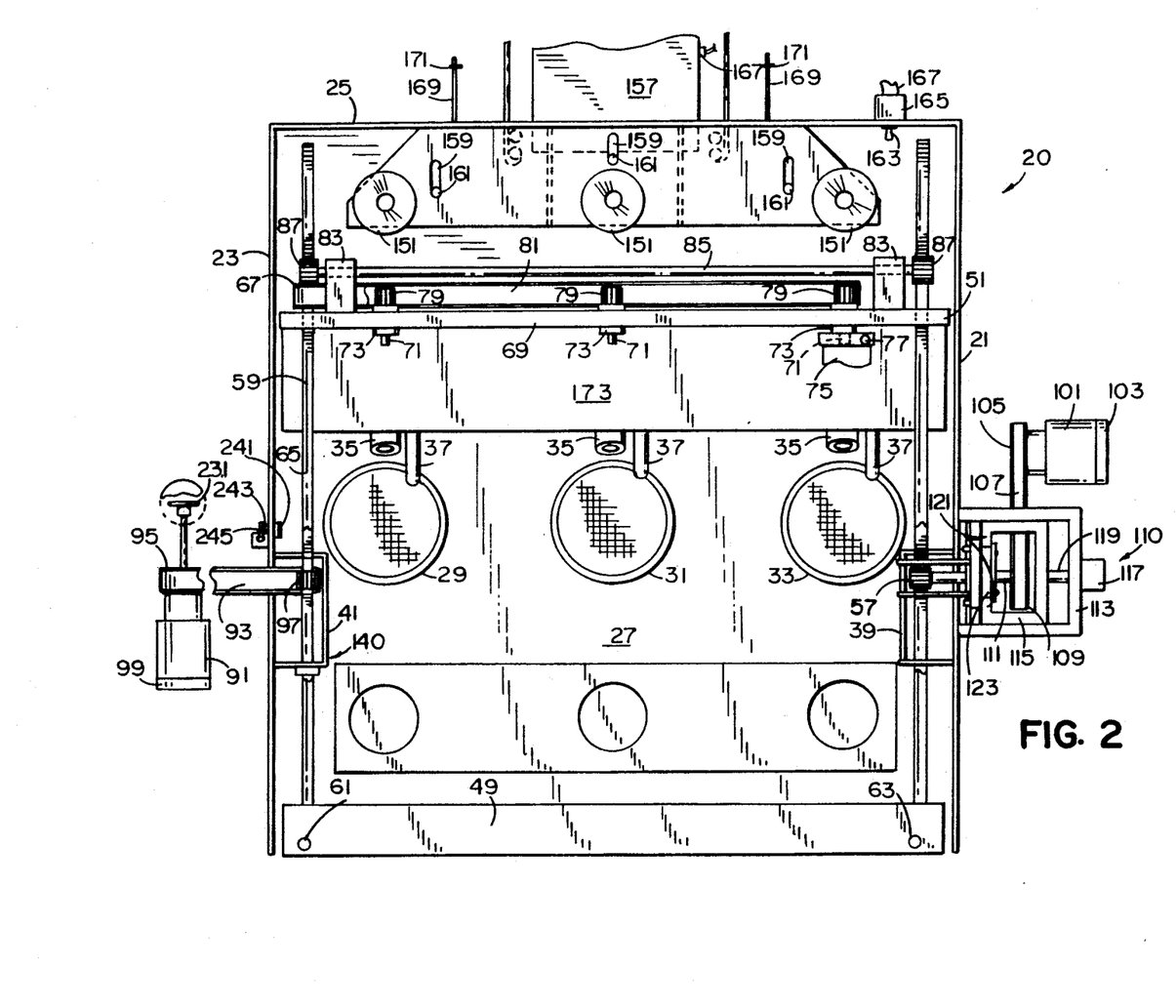
FIG. 2 is a top plan view of the apparatus.
Figure 3:
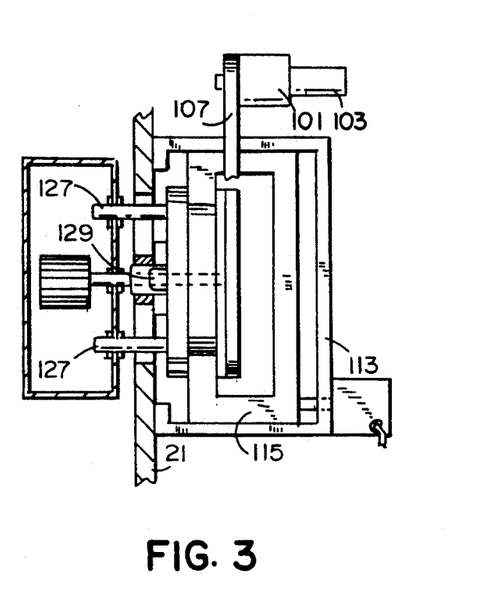
FIG. 3 is a sectional view of the clutch assembly.
Figure 4:
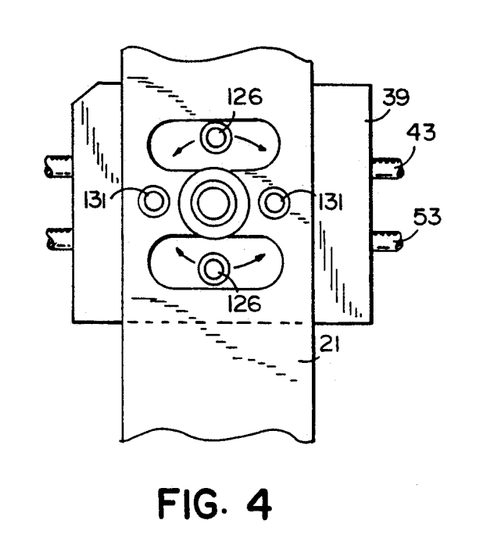
FIG. 4 is an elevational view showing the bushings in the journal block and frame.
Figure 16:
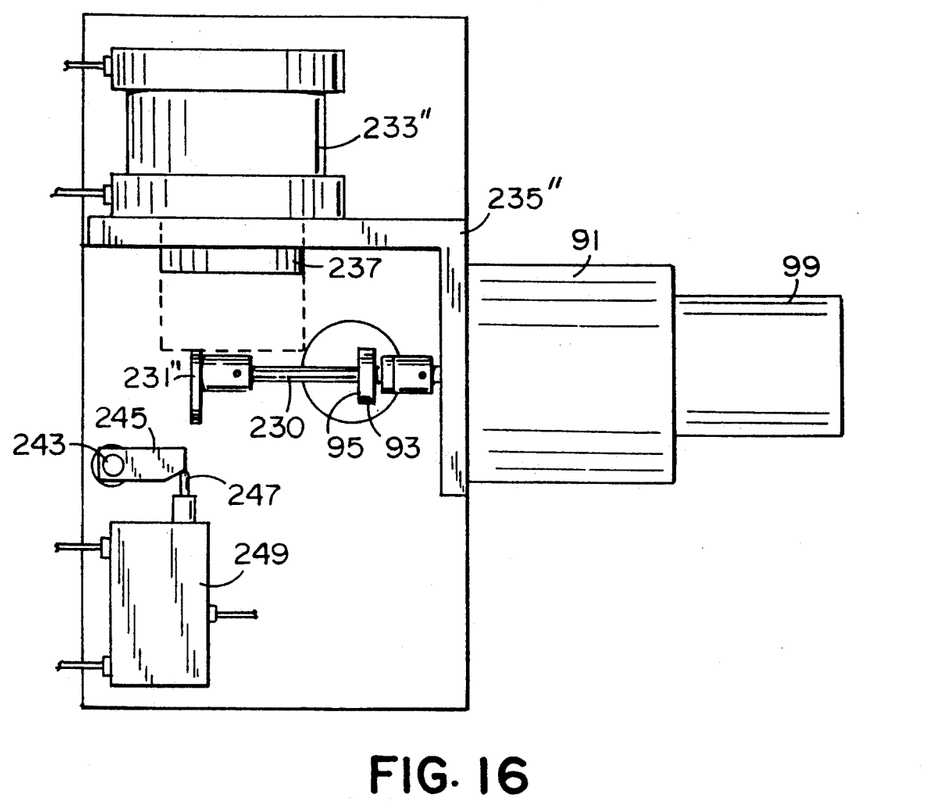
FIG. 16 is an elevational view of the interlock assembly which prevents the crucibles from pouring over the burners.
Figure 17:
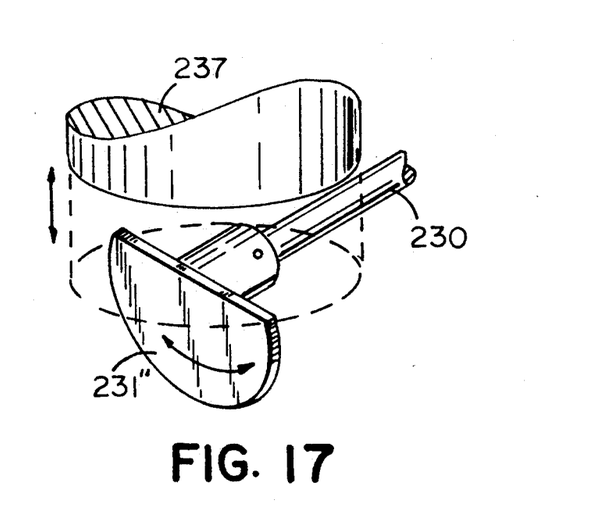
FIG. 17 is an enlarged view of the portion of the interlock circled in FIG. 2.
Figure 18:
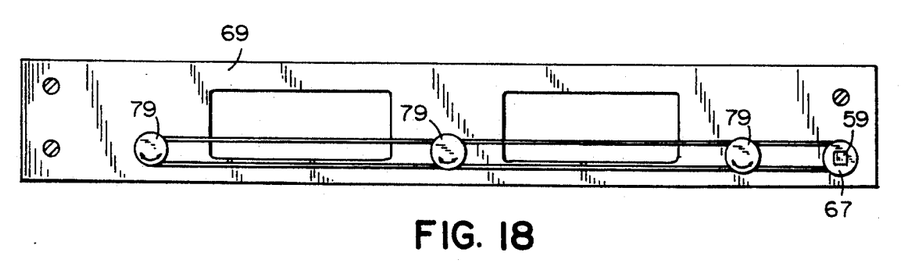
FIG. 18 is a rear view of movable subassembly.

As previously discussed, nothing is added to or poured from the crucible while it is over a burner. Referring to FIG. 16, the interlock circuit is shown which prevents the apparatus used to horizontally rock the crucibles from pouring the contents of a crucible out while it is being heated. As previously discussed, servo motor 91, equipped with shaft encoder 99, controls the horizontal rocking of the crucibles. Servo motor 91 has an output shaft 230 upon which sprocket 95 is mounted. Continuous chain 93 is trained over sprocket 95 and connects to gear 97 mounted on square shaft 65 (FIG. 2). On the end of shaft 230, a limit member in the form of a semicircle of metal 231" is mounted. A pneumatic cylinder 233" is mounted on frame 235". Cylinder 233" has a movable piston 237, which extends downwardly above limit member 231". The oscillation of shaft 230 and limit member 231" is controlled by shaft encoder 99 and the control circuitry of the apparatus. The limit member 237 does not come into contact with piston 237 during normal operation. If there is a problem in the control circuitry, and motor 91 attempts a complete revolution which would dump the contents of the crucible into the burner, limit member 91 will strike piston 237 stopping the motor from turning and protecting the burner.

Now referring to FIG. 2, a finger 241 extends downwardly through an aperture in sidewall 23. Finger 241 is connected to a shaft 243 which, in turn, is coupled to an actuating arm 245. When it is time to pour the contents out of the crucible, the main burners are turned off and subassembly 51 moves toward the front of the machine to bring crucibles to station 180. Front plate 69 of subassembly 51 strikes finger 241 causing arm 245 to press pin 247 on valve 249 which activates pneumatic cylinder 233, causing piston 237 to retract from limit member 231. Motor 91, now under the control of the apparatus electronics, can rotate pouring the contents out of the crucible into the appropriate casting dish or beaker for analysis.

From the above description it can be seen that the main burners of the apparatus are now protected from accidental spills of either the molten material in the crucibles or of any additional materials such as wetting agents which might be added to the crucibles. Also, the mixing pattern of the crucibles is made variable to fit the characteristics of the particular sample by the simple procedure of adjusting the extent of movement of servo motors 91 and 101.

Although the invention has been described with respect to specific preferred embodiments thereof, many variations and modifications will become apparent to those skilled in the art. It is, therefore, the intention that the appended claims be interpreted as broadly as possible in view of the prior art to include all such variations and modifications.

The embodiments of the invention in which an exclusive property or privilege is claimed are defined as follows:

1. An apparatus for mixing the contents of a heated crucible comprising:
    a main frame including a pair of horizontally spaced shafts;
    a first and a second block, each of said blocks carried on opposite sides of a supporting frame, each of said blocks movably supporting one of said horizontally spaced shafts;
    a counter balance attached to and extending between the same ends of each of said horizontally spaced shafts;
    a movable subframe supported on an extending between each of said horizontally spaced shafts, said movable subframe including:
    a panel;
    a plurality of rotatable shafts supported on said panel, each of said shafts having a first and a second end, said first end projecting through said panel for supporting a crucible holder, a sprocket mounted on said second end of each of said rotatable shafts;
    a driving gear rotatably supported on said panel near one end thereof;

a continuous chain trained around said driving gear and each of said sprockets on said rotatable shaft;

a driving shaft for said driven gear, said driving shaft being slidably disposed in said driven gear and being rotatably mounted in one of said first pivotally mounted blocks;

a first motor operatively connected to said driving shaft for causing said driving shaft and each of said rotatable shafts supported by said panel to oscillate;

a rack connected to said panel on said subframe and extending through said second block;

a pinion gear supported in said second block and operatively connected to said rack for moving said rack and said subframe on said horizontally spaced shafts; and a second motor operatively connected to said second block for causing said second block and said main frame to oscillate in a vertical direction and for causing said pinion to move said rack and said subframe forward and backward on said horizontally spaced shafts.

2. An apparatus as set forth in claim 1, wherein each of said first and second motors is a servo motor and the movement of each motor is controlled for varying the mixing of the contents of a crucible supported on said subframe.

3. An apparatus as set forth in claim 1, wherein said first motor causes a supported crucible to oscillate in a horizontal plane and said second motor causes a supported crucible to rock in a vertical plane.

4. An apparatus as set forth in claim 1, including:
a shaft extending from said first motor;
a limit member supported on said shaft of said first motor;
a pneumatic cylinder including a movable piston mounted near said limit member, said piston limiting the rotation of said limit member during the mixing of the contents in said crucible;
a valve for actuating said pneumatic cylinder to move said piston away from said limit member to enable said limit member to rotate; and
an actuator for said valve positioned to be contacted by said movable subframe as it moves on said main frame from the mixing position to a position where the contents of said crucible are poured out.

5. An apparatus as set forth in claim 4, wherein said limit member is a semicircle having a flat side facing said piston during mixing and a curved side facing said piston during the pouring out of the contents of said crucible.

6. An apparatus as set forth in claim 1, wherein:
said second motor is operatively coupled to a driving gear operatively coupled to said second motor;
a clutch operatively coupled to said driving gear, said clutch having a first and a second position, in said first position said clutch couples said driving gear to said second pivotally mounted block to cause said block to oscillate, in said second position said clutch locks said second block to the supporting frame enabling said driving gear to rotate said pinion gear to move said subframe either forward or backward on said main frame.

7. An apparatus as set forth in claim 1, further including a material addition apparatus carried on the supporting frame, said material addition apparatus including:
a first plate and a contiguous second plate slidably coupled together, said second plate having a plurality of spaced apertures near one edge thereof;
a plurality of material holders supported in said apertures in said second plate, said material holders having an open bottom closed by said first plate;
a driver coupled to said second plate for causing said first and second plates to move; and
a stop for stopping the movement of said first plate while said second plate and said material holders continue to be moved by said driver causing the open bottoms of said material holders to move away from said first plate enabling the contents of said material holders to fall through said open bottoms.

8. An apparatus as set forth in claim 7, wherein said material holders are funnel-shaped.

9. An apparatus as set forth in claim 7, wherein said second plate has a plurality of spaced slots, a plurality of fasteners extend through said slots to support said first plate in sliding engagement with said second plate.

10. An apparatus for mixing the contents of a heated crucible, comprising:
a main frame including a pair of horizontally spaced shafts;
a first block and a second block, each of said blocks carried on a supporting frame and movably supporting a respective one of said horizontally spaced shafts;
a moveable subframe supported on said shafts, said moveable subframe supporting a plurality of crucible holders and a driver operatively coupled to said crucible holders;
a motor operatively coupled to said driver for causing said driver and said crucible holders to oscillate;
a rack coupled to said moveable subframe and extending through one of said first and second blocks;
a gear supported in said one of said blocks operatively coupled to said rack; and
a second motor operably connected to said one of said blocks for causing said one block and said main frame to oscillate in a vertical direction and for causing said gear to move said rack and said subframe forward and backward on said horizontally spaced shafts.

* * * * *